US005111809A

United States Patent [19]

Gamble et al.

[11] Patent Number: 5,111,809

[45] Date of Patent: May 12, 1992

[54] BREATHING SYSTEM

[75] Inventors: Bruce B. Gamble, West Hartford; Douglas A. Snowdon, Somers, both of Conn.

[73] Assignee: Avstar Aerospace Corporation, North York, Canada

[21] Appl. No.: 278,399

[22] Filed: Dec. 1, 1988

[51] Int. Cl.[5] .......... A61M 16/00

[52] U.S. Cl. .......... 128/204.18; 128/204.26; 128/205.11; 128/205.14; 128/205.15

[58] Field of Search .......... 128/204.18, 204.15, 128/204.26, 204.28, 205.11, 205.12, 205.13, 205.14, 205.15, 205.16, 205.17, 205.24

[56] References Cited

U.S. PATENT DOCUMENTS

| | | | |
|---|---|---|---|
| 2,969,789 | 1/1961 | Mörch | 128/205.14 |
| 3,266,488 | 8/1966 | Andreasen | 128/205.15 |
| 3,292,617 | 12/1966 | McDonough | 128/205.15 |
| 3,307,542 | 3/1967 | Andreasen | 128/205.15 |
| 3,339,545 | 9/1967 | Burchell | 128/205.14 |
| 3,489,144 | 1/1970 | Dibelius | 128/205.12 |
| 3,537,450 | 11/1970 | Fox | 128/205.14 |
| 3,540,443 | 11/1970 | Huddy | 128/205.17 |
| 3,566,867 | 3/1971 | Dryden | 128/205.28 |
| 3,650,269 | 3/1972 | Curtis | 128/202.26 |
| 3,695,261 | 10/1972 | Emmons | 128/204.22 |
| 3,794,021 | 2/1974 | Lambertsen | 128/204.28 |
| 3,794,021 | 2/1974 | Lambertsen | 128/205.17 |
| 3,794,030 | 2/1974 | Cotabish et al. | 128/202.26 |
| 3,863,629 | 2/1975 | Ries | 128/205.12 |
| 3,908,649 | 9/1975 | Eckstein | 128/201.13 |
| 3,910,780 | 10/1975 | Henley et al. | 128/205.28 |
| 3,916,889 | 11/1975 | Russell | 128/205.15 |
| 3,973,564 | 8/1976 | Carden | 128/205.14 |
| 4,005,708 | 2/1977 | Netteland et al. | 128/205.28 |
| 4,048,993 | 9/1977 | Dobritz | 128/201.13 |
| 4,168,706 | 9/1979 | Lovell | 128/202.26 |
| 4,193,966 | 3/1980 | Dowgul | 422/122 |
| 4,340,044 | 7/1982 | Levy et al. | 128/205.15 |
| 4,811,732 | 3/1989 | Hartung | 128/205.14 |

OTHER PUBLICATIONS

The Sodasorb Manual.

ASME-A Portable Oxygen Subsystem-Description and Preliminary Thermal Performance Prediction by F. Sribnik.

*Primary Examiner*—David A. Wiecking

*Assistant Examiner*—Aaron J. Lewis

*Attorney, Agent, or Firm*—Rogers, Bereskin & Parr

[57] ABSTRACT

A respiratory apparatus, which receives exhaled gas from a user, removes carbon dioxide from and introduces oxygen into the exhaled gas, to present a breathing gas to a user. A respiratory flow transducer in the respiratory apparatus is subjected to the breathing gas demand of the user. Oxygen is introduced into the breathing system by an oxygen flow regulator connected to an oxygen supply inlet. The respiratory flow transducer and the oxygen flow regulator are connected by a linkage. The linkage constrains the oxygen flow regulator and respiratory flow transducer to operate together whereby there is a substantially constant ratio between the breathing gas flow rate and the oxygen flow rate.

An air bleed system can be connected to an air inlet to introduce air into the respiratory apparatus and to displace a portion of the gas from the respiratory apparatus. The air bleed system ensures a relatively constant oxygen concentration in the breathing gas presented to the user despite varying oxygen demands placed upon the respiratory apparatus by the user.

29 Claims, 3 Drawing Sheets

BREATHING SYSTEM

FIELD OF THE INVENTION

This invention relates to methods and apparatus for providing a breathable gas mixture for use in a hostile environment and, more particularly, to a re-breather system in which oxygen introduction is controlled.

BACKGROUND OF THE INVENTION

Portable breathing systems are used to enable their user's to function in an environment which lacks oxygen or in an environment containing substances which would be toxic if inhaled. For example, they are used in industrial plants where toxic chemicals have been spilled, or where there is a fire, e.g. in a mine. Various breathing systems are known, these systems can be divided into three broad categories.

A first category are those systems which provide a breathable gas to the user and in which the user's exhalate is exhausted out of the system i.e. the system is open. Such systems typically use compressed air or a compressed blend of oxygen and nitrogen. Such compressed air systems are advantageous both in cost and weight in circumstances where a separate compressed air supply not carried by the user is readily available and where length of a supply hose is not a limiting factor. Compressed air systems have a weight disadvantage over the other systems when the compressed air source of the system is made portable. As all of the consumed air in a compressed air system is exhaled from the system, these systems have the highest gas consumption for a given operating duration.

Another type of breather system is such as described in U.S. Pat. No. 3,794,030 entitled "EMERGENCY BREATHING APPARATUS" which issued Feb. 26th, 1974. In this type of breathing system, exhaled gas rather than being discharged from the system is passed through a chemical bed of, for example, potassium superoxide and then released to the user, i.e. the system is closed. The superoxide reacts with the exhaled gas to remove carbon dioxide therefrom and at the same time to release oxygen which will mix with the exhaled gas to revitalize the exhaled gas for rebreathing. A disadvantage with this type of system is that considerable heat is generated by the chemical reaction.

A third general category of breathing systems are those in which the exhaled gas is treated by removing carbon dioxide from it and adding oxygen to it to replenish the oxygen consumed by the user. Again, this is a closed system. A problem with this type of a system is to maintain a relatively constant concentration of oxygen. If too much oxygen is added to such a system, the system eventually becomes oxygen rich and any gas leakage from around the connection between the system and the user's face, or elsewhere, could be quite hazardous in a combustible environment. If not enough oxygen is added to the rebreathed gas, the user will, of course, suffer from oxygen shortage. It is possible to use an oxygen probe to monitor the oxygen concentration in the system and thereby electronically control the amount of oxygen added to the system. Disadvantages with such an electronic oxygen control system are the attendant cost and as well the increased likelihood of failure. Adding an electrical system to what would otherwise be a purely mechanical system introduces another system along with its attendant risk of failure.

SUMMARY OF THE INVENTION

This invention provides a respiratory apparatus for supplying breathing gas to a user. The apparatus has a respiratory circuit which includes a first variable volume chamber which expands and contracts during exhalation and inhalation respectively. The apparatus further has a connection means for supplying breathing gas to and receiving exhaled gas from a user. The apparatus has a respiratory flow transducer which is subjected to the breathing gas demand by the user. An oxygen flow regulator is connected to the respiratory circuit for introducing oxygen into the respiratory circuit. The oxygen flow regulator is connected to an oxygen supply inlet and receives oxygen from this inlet. A linkage means connects the respiratory flow transducer and the oxygen flow regulator together to constrain the respiratory flow transducer and oxygen flow regulator to operate together, whereby, there is a substantially constant ratio between the breathing gas flow rate and the oxygen flow rate.

BRIEF DESCRIPTION OF THE DRAWINGS

Reference will now be made to the accompanying drawings which illustrate a preferred embodiment of the invention by way of example, and in which.

DESCRIPTION OF THE PREFERRED EMBODIMENT

Figure 1:
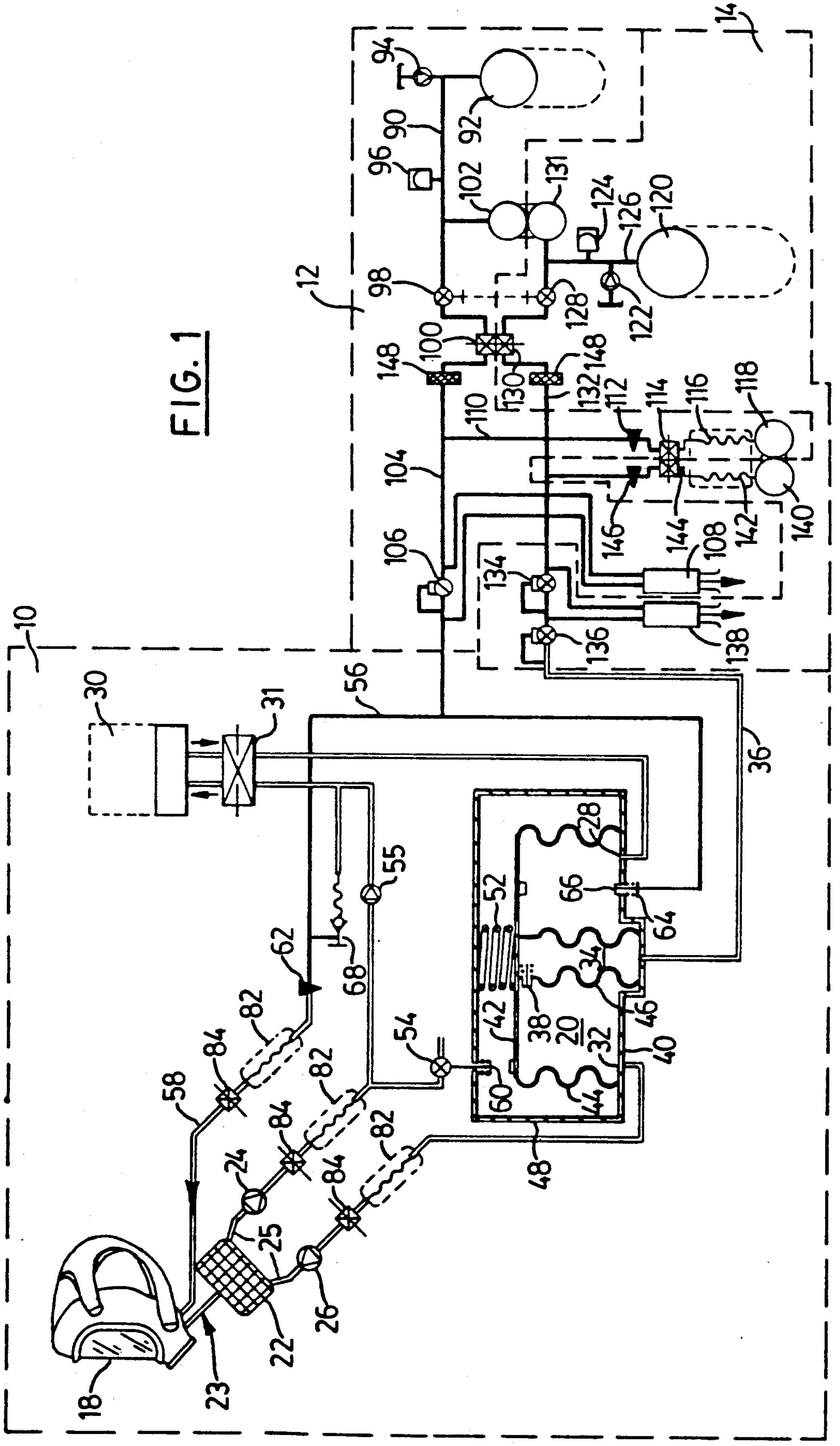
FIG. 1 is a schematic representation of the breathing system according to a first embodiment of the present invention, showing in cross section first and second variable volume chambers.

Referring to FIG. 1, the breathing system identified generally by reference 10 is shown attached to an air supply system 12 and an oxygen supply system 14 (indicated by broken lines). Exemplary air and oxygen systems 12 and 14 are shown. Any air supply and oxygen supply system which will produce the required pressure and amount of air or oxygen respectively to the system and as well, has the required safety features, can be used with the breathing system of the present invention, to form a complete respiratory apparatus.

The first embodiment of the breathing system illustrated in FIG. 1 uses a face mask 18 as a connection means between the user and the breathing system. The face mask 18 includes an oral/nasal cup (not shown). The mask 18 supplies breathing gas to and receives exhaled gas from the user through the oral/nasal cup. While a face mask is desirable as a connection means in that it enables air to be supplied to the entire face of the user, including the user's eyes, nose and mouth, it will be understood that other connection means such as a mouthpiece or an oral/nasal cup on its own without a face mask could alternatively be used.

Exhaled gas is introduced into the breathing system 10 by the user, through the connection means or face mask 18. From the face mask 18, exhaled gas passes through the breathing system 10 where carbon dioxide is removed from the exhaled gas and oxygen is introduced to provide a breathing gas suitable for inhalation by the user. The flow of gas through the breathing system 10 of the preferred embodiment is unidirectional being controlled by an exhalation valve 24 and an inhalation valve 26 which are one-way valves. The flow of gas through the breathing system, both into and out of the system, commencing at the face mask, defines a respiratory circuit.

The face mask 18 is fluidly connected with a first variable volume chamber 20 so that exhaled gas received by the face mask will enter the first variable volume chamber 20 through an exhaled gas inlet 28. A positive pressure at the exhaled gas inlet 28 will cause the variable volume chamber 20 to expand thereby admitting the exhaled gas.

In order to remove carbon dioxide from the exhaled gas, a carbon dioxide removal canister 30 is interposed between the face mask 18 and the exhaled gas inlet 28. The carbon dioxide removal canister 30 removes carbon dioxide from the exhaled gas prior to its entry into the variable volume chamber 20. Carbon dioxide removal can be achieved using known means such as alkali or alkaline metal hydroxide absorption. The canister 30 is connected by a connector 31, permitting ready removal and attachment of a fresh canister 30.

The first variable volume chamber 20 is also fluidly connected to the face mask 18 through an inhalation outlet 32. Upon inhalation by the user, gas is withdrawn from the first variable volume chamber 20 through the inhalation outlet 32 and into the face mask 18. This withdrawal of gas causes the first variable volume chamber 20 to contract.

It will be appreciated that the breathing circuit could be a to and fro circuit rather than a unidirectional circuit, a unidirectional circuit as illustrated in FIG. 1, is preferred as such a unidirectional circuit prevents rebreathing of exhaled air prior to carbon dioxide removal or oxygen replenishment.

Alkali or alkaline metal hydroxide carbon dioxide absorbants typically generate a considerable amount of heat and as well, they work more effectively under high heat and high humidity conditions. A user of a rebreather system would typically be uncomfortable if subjected to the heat and humidity in the breathing gas that is required for optimum operating conditions of the carbon dioxide absorption system. To accommodate both the user's comfort requirements and the desired temperature and humidity range for carbon dioxide removal, a heat exchanger 22 has an inlet 23 that is fluidly connected to the face mask 18 and outlets 25 connected to the valves 24, 26. The heat exchanger 22 is of a regenerative type and heats and humidifies exhaled air while cooling and dehumidifying the breathing gas. During inhalation, hot humid air, originating from the carbon dioxide canister 30, is drawn from the variable volume chamber 20 and through heat exchanger 22 to heat the exchanger, a process which cools the breathing gas and causes moisture to condense in the heat exchanger. On a subsequent exhalation, the exhaled gas, in passing through the heat exchanger, will be heated and will pick up the condensate from the heat exchanger through evaporation. This ensures that the breathing gas is of a suitable temperature and humidity for user. Also, the breathing circuit is maintained at an elevated temperature, which improves the efficiency of the carbon dioxide absorption and promotes necessary heat dissipation from the breathing circuit.

In order to revitalize the gas in the respiratory circuit to render it breathable by the user of the respiratory apparatus, it is necessary to introduce oxygen into the respiratory circuit. One system for introducing oxygen into the respiratory circuit so that there is a substantially constant ratio between the breathing gas flow rate and the oxygen flow rate is shown in FIG. 1.

The first variable volume chamber 20 illustrated in FIG. 1 has an outer or first expansive cylinder 44 concentric with an inner or second expansive cylinder 46. Both the outer and inner expansive cylinders 44 and 46 respectively are sealed at one end to a fixed bottom 40 and at the opposite end to a movable, disc-shaped, platen 42 (both of the cylinders 44, 46 are formed as flexible, convoluted walls). As the platen 42 and the fixed bottom 40 extend across both the outer and inner expansive cylinders 44 and 46 respectively, it will be appreciated that a second variable volume chamber 34 is defined by the inside of inner expansive cylinder 46, platen 42 and the fixed bottom 40. In the arrangement shown in FIG. 1, the first variable volume chamber 20 is of generally annular configuration, defined by the two cylinders 44, 46, the fixed bottom 40 and the platen 42. The second variable volume chamber 34 is contained with the first variable volume chamber 20 and is concentric therewith.

Introduction of gas to, or removal of gas from, the first variable volume chamber 20 will cause the platen 42 to move respectively away from or toward the fixed bottom 40. In this arrangement, the first variable volume chamber 20 acts as a respiratory flow transducer in that exhalate gas introduction into the respiratory circuit, or breathing gas demand placed upon the respiratory circuit, are translated into movement of the platen 42.

As the platen 42 is common to both the first variable volume chamber 20 and the second variable volume chamber 34, platen 42 also acts as a linkage means connecting the first and second variable volume chambers 20 and 34 respectively. Thus, movement of the platen 42, will cause the second variable volume chamber 34 to expand or contract accordingly.

In the embodiment illustrated in FIG. 1, the second variable volume chamber 34 is connected to the oxygen supply system 14 by an oxygen inlet line 36. The second variable volume chamber 34 is fluidly connected with the first variable volume chamber 20 through an oxygen admission valve 38. The oxygen admission valve 38 is a spring-biased, normally closed, one-way valve which can be opened by pressure in the second variable volume chamber 34 to permit oxygen to flow from the second variable volume chamber 34 into the first variable volume chamber 20. In this embodiment, the second variable volume chamber 34 and the oxygen admission valve 38 act together as an oxygen flow regulator. Expansion of the second variable volume chamber 34 admits oxygen into this chamber. As the volume of the second variable volume chamber 34 is diminished, the oxygen contained therein will be compressed. As the oxygen system 14 prevents backflow, this causes the oxygen admission valve 38 to open to admit oxygen into the first variable volume chamber 20. The oxygen system 14 would typically be a high pressure system with a pressure regulator at its outlet to reduce and regulate the pressure presented to the oxygen inlet 36. The higher pressure upstream from the oxygen pressure regulator prevents oxygen from flowing back through the oxygen inlet 36 instead of through the oxygen admission valve 38.

The volume of the first and second variable volume chambers, 20 and 34 respectively, would vary directly with their respective heights. As the heights of the first and second variable volume chambers, 20 and 34 respectively, vary together and in the same amount, it will be appreciated that their respective volumes will vary in a substantially constant ratio. In this manner, a substantially constant ratio between the breathing gas flow rate and the oxygen flow rate will be maintained. Thus, oxygen should be supplied at a rate corresponding to the user's work rate.

Oxygen could be supplied directly from the second variable volume chamber 34 to the face mask. A disadvantage with supplying oxygen directly to the face mask 18, however, is the safety risk inherent in pure oxygen escaping from the face mask when the respiratory apparatus is used in a combustible environment.

To ensure a positive pressure in the respiratory circuit, a biasing means which urges the first variable volume chamber toward a reduced volume is used. One such biasing means is illustrated in FIG. 1 which shows the first and second variable volume chambers, 20 and 34 respectively, as being contained within a housing 48. The housing 48 has a top 50 above the platen 42. A spring 52 inserted between the top 50 and the platen 42 urges the platen toward the fixed bottom 40 to provide a positive pressure. Alternatively, instead of using the spring 52, the region defined by the inside of housing 40, the outside of the outer expansive cylinder 44 and the top of the platen 42 could be pressurized. Pressurizing this region would urge the platen 42 toward the fixed bottom 40 to provide a positive pressure in the respiratory circuit.

An air bleed system is incorporated in the embodiment illustrated in FIG. 1. The air bleed system comprises: an air inlet 56 fluidly connected through a bleed air line 58 to the face mask 18; a normally closed vent valve 54 connected to a connection conduit between the exhalation valve 24 and the carbon dioxide canister 30; an actuator 60 for the normally closed vent 54 fixed above the platen 40; and, an orifice 62 between the face mask 18 and the air inlet 56. Additionally, a non-return valve 55 is provided to prevent backflow from the carbon dioxide removal canister during venting through the valve 54. The air bleed system ensures a relatively constant oxygen concentration in the breathing gas despite various breathing gas and oxygen demand rate requirements. The operation of this system is described below.

To connect the exhalation and inhalation valves 24, 26 and the bleed airline 58 to the rest of the respiratory circuit, respective flexible hoses 82 and connectors 84 are provided.

Pressurized air from the air system 12 is presented to the air inlet 56 at a constant pressure. The orifice 62 in the fluid connection between the air inlet 56 and the face mask 18 ensures a constant flow rate of air to the face mask 18. The air is introduced into the mask 18 outside the oral/nasal cup. Although air can be introduced anywhere into the respiratory circuit, it is desirable to introduce air directly into the face mask 18 as this serves to reduce fogging of the face mask 18, the air being cool and dry, and to present a more comfortable environment to the user within the face mask 18. Also, it ensures that gas escaping from the periphery of the mask 18 is not rich in oxygen. Air entering the face mask 18 from the air bleed system is drawn into the oral/nasal cup through suitable valves and is inhaled by the user and will form part of the exhaled gas introduced by the user into the respiratory circuit. The presentation of air to the user in addition to the breathing gas provided by the respiratory circuit will eventually cause the first variable volume chamber to expand to its maximum capacity of volume. When this predetermined maximum volume has been attained, the top of platen 42 will strike the vent actuator 60 causing the vent 54 to open. Once the vent 54 is opened and the first variable volume chamber has reached its maximum volume, any additional exhalate will exit from the respiratory circuit through the vent 54. Upon subsequent inhalation by the user, the volume of the first variable volume chamber 20 will, of course, decrease drawing the platen 42 away from the vent actuator 60, thereby closing the vent 54. In this manner, a portion of the gas in the respiratory circuit is removed on each breathing cycle. The amount of gas removed is approximately equal to the volume of air being introduced into the face mask through the air bleed system.

The variation in oxygen concentration arising from different ratios of oxygen use to breathing flow rates will decrease as the volume of air introduced through the air bleed system increases. The oxygen flow regulator can therefore be sized to introduce the maximum ratio of oxygen flow to breathing flow which it would be anticipated that a user could consume. Sizing the oxygen flow regulator to introduce an amount of oxygen flow equalling approximately 6% of the breathing flow should be adequate for a variety of users under most circumstances. The air flow rate through the air bleed system can then be used to ensure that the oxygen concentration in the breathing gas presented to the user at the face mask does not exceed a level which is safe under the circumstances of use.

The volume flow rate of air introduced to the respiratory circuit can be controlled either by varying the size of orifice 62 or by using an alternative air volume controller, such as a variable valve, in lieu of the orifice 62.

As a substantial portion of the breathing gas supplied by the system as described above comprises exhaled gas from which carbon dioxide has been removed and into which oxygen has been introduced, it will be appreciated that this respiratory apparatus will consume less gas than would be consumed by an open system relying entirely on compressed air. Additionally, this respiratory apparatus ensures a more constant oxygen concentration at the face mask 18 than would be possible if the system used only oxygen without the air bleed system.

Depending on the size of the first variable volume chamber 20 and the capacity of the user's lungs, it is conceivable that a user might completely exhaust the first variable volume chamber 20. In order to prevent the user's breathing gas supply from being cut off should the user completely exhaust the first variable volume chamber 20, a make-up air system is also provided in the embodiment shown in FIG. 1. The make-up air system comprises a normally closed air inlet valve 64 in the first variable volume chamber 20, the air inlet valve 64 being fluidly connected with the air inlet 56 of the air supply 12 and being actuated by an air inlet valve actuator 66 fixed below the platen 42. In use, when the first variable volume chamber 20 is completely exhausted or reaches a predetermined minimum volume. the platen 42 strikes the air inlet valve actuator 66 which in turns opens the air inlet valve 64. Opening of the air inlet valve 64 allows make-up air to enter into the first variable volume chamber 20 from the air system 12. This make-up air will pass through the first variable volume chamber 20 exiting through the inhalation outlet 32 to be presented to the user. In this way, breathing gas will be supplied to the user despite the exhaustion of the first variable volume chamber.

Although for the reasons described above, it is desirable to introduce bleed air to the face mask, in an alternative embodiment, the volume of the first variable volume chamber could be such that bleed air would be introduced into the first variable volume chamber 20 as make-up air on each inhalation cycle, thereby doing away with the air bleed directly to the face mask.

As it may be desirable to purge the respiratory circuit if it is thought that the circuit is contaminated, an air purge valve 68 is provided. The air purge valve 68 is fluidly coupled with the air inlet 56 and with the inlet to the carbon dioxide removal canister 30. Opening the air purge valve 68 will admit air from the air inlet 56 into the respiratory circuit to flow through the respiratory circuit thereby purging the respiratory circuit.

FIGS. 2, 3, 4 and 5 show alternate embodiments with slightly different configurations for the first and second variable volume chambers and their respective platens. Similar components to those described above are similarly labelled. Also, for simplicity, not all the elements are shown; thus, in FIGS. 2 and 3 for example the ventilation valve 54 is omitted.

Figure 2:
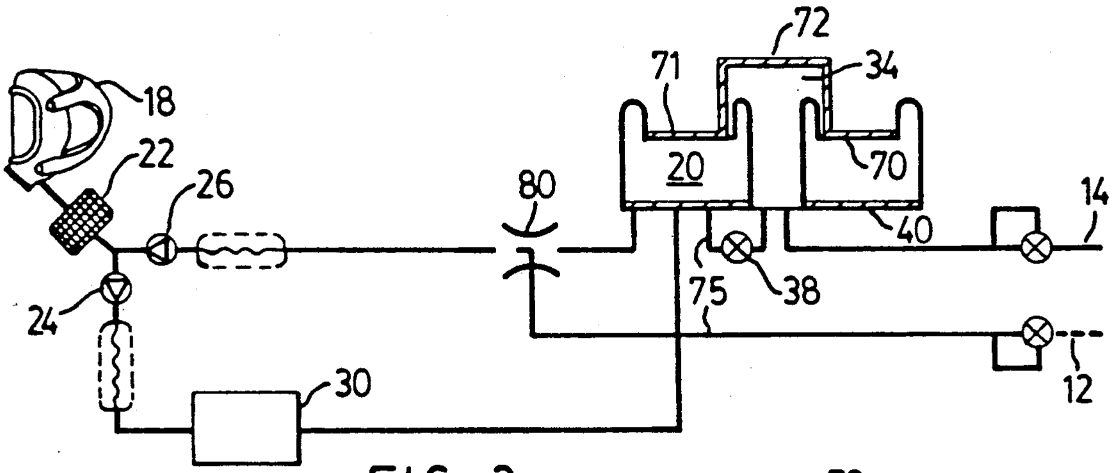
FIG. 2 is a cross-sectional view of a second embodiment of the first and second variable volume chambers of the invention.

In FIG. 2, the first variable volume chamber 20 has a substantially cup-shaped platen 70 comprising a first, central circular post 72 closing off one end of the second variable volume chamber 36 and a second, annular post 71 closing off one end of the annular first chamber 20. In the embodiment shown in FIG. 2, oxygen introduction from the second variable volume chamber 34 into the first variable volume chamber 20 is through an external conduit 73, fluidly connecting the bottom of the first variable volume chamber 20 with that of the second variable volume chamber 34. The oxygen admission valve 38 is interposed in the conduit 73 between the first and second variable volume chambers 20 and 34 respectively. The platen 70 is not biased in any way. In order to maintain a positive pressure in the face mask 18 an inductor 80 is provided, which is connected to the air supply system 12. To prevent continuous flow through the face mask 18, the exhalation valve 24, in this embodiment, has an offset equal to the pumping head of the inductor 80.

Figure 3:
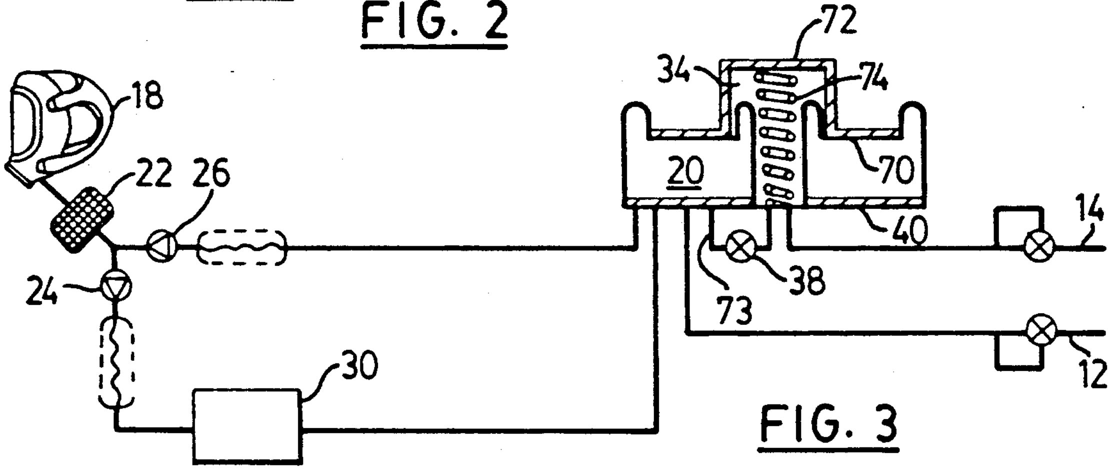
FIG. 3 is a cross-sectional view of a third embodiment of the first and second variable volume chambers including a biasing spring.

In the embodiment shown in FIG. 3, a spring 74 is attached to the cup-shaped platen 70 and the fixed bottom 40. The spring 72 biases the cup-shaped platen 72 toward the fixed bottom 40 and in turn biases the annular platen 70 toward the fixed bottom 40 to ensure positive pressure within the respiratory circuit. The inductor 80 and offset for the valve 24 are then no longer required.

Figure 4:
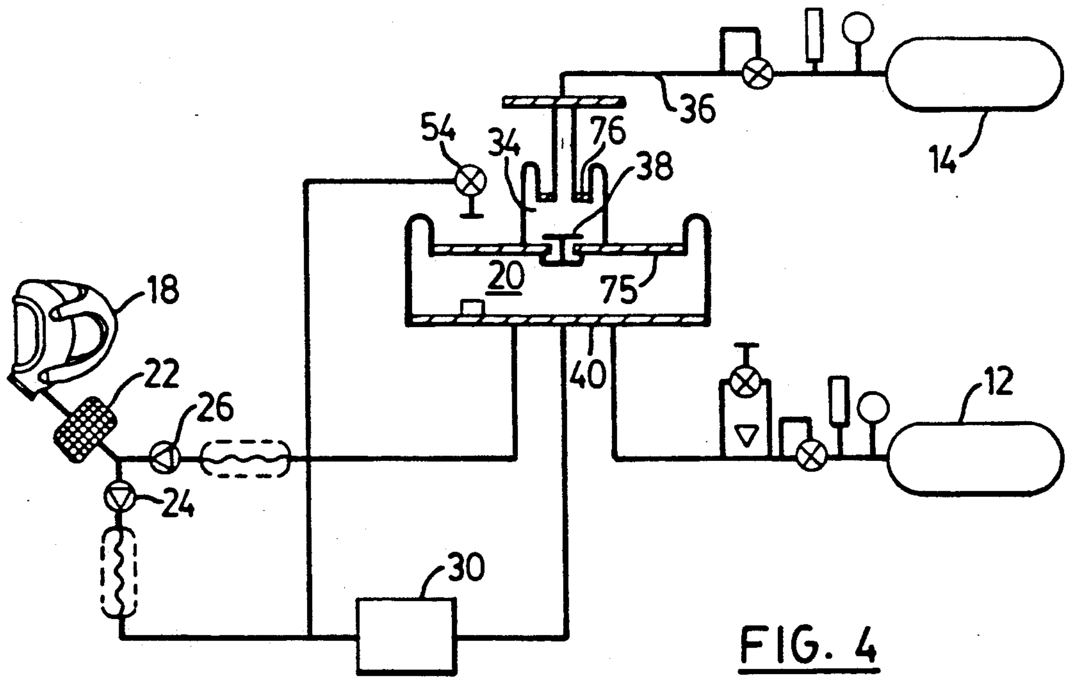
FIG. 4 shows a fourth embodiment of the first and second variable volume chambers of the present invention.

In the embodiment shown in FIG. 4, the second variable volume chamber 34 surmounts the first variable volume chamber 20 rather than being contained therein. In this configuration oxygen is admitted to the first variable volume chamber 20 during expansion of the first variable volume chamber 20 rather than during contraction of the first variable volume chamber 20 as in the embodiments described above. In this embodiment, the top 76 of the variable volume chamber 34 is of inverted T shaped configuration and is held fixed. Oxygen is admitted to the second variable volume chamber 34 through a cylindrical passage in the stem of the T. A disc-shaped platen 75 defines the top of the first variable volume chamber 20 and as well the bottom of the second variable volume chamber 34. In this embodiment, the top 76 of the second variable volume chamber 34 and the fixed bottom 40 are held equidistant. A positive pressure in the second variable volume chamber 34 therefore acts against the disc-shaped platen 75 to bias it toward the fixed bottom 40 of the first variable volume chamber 34. This biasing of the disc-shaped platen 75 by the oxygen pressure will ensure a positive pressure in the respiratory circuit. This embodiment does away with the requirement for a spring to act on the platen 75 to produce a positive pressure in the respiratory circuit. The valve 38 is provided in the platen 75 between the two variable volume chambers 20, 34.

Figure 5:
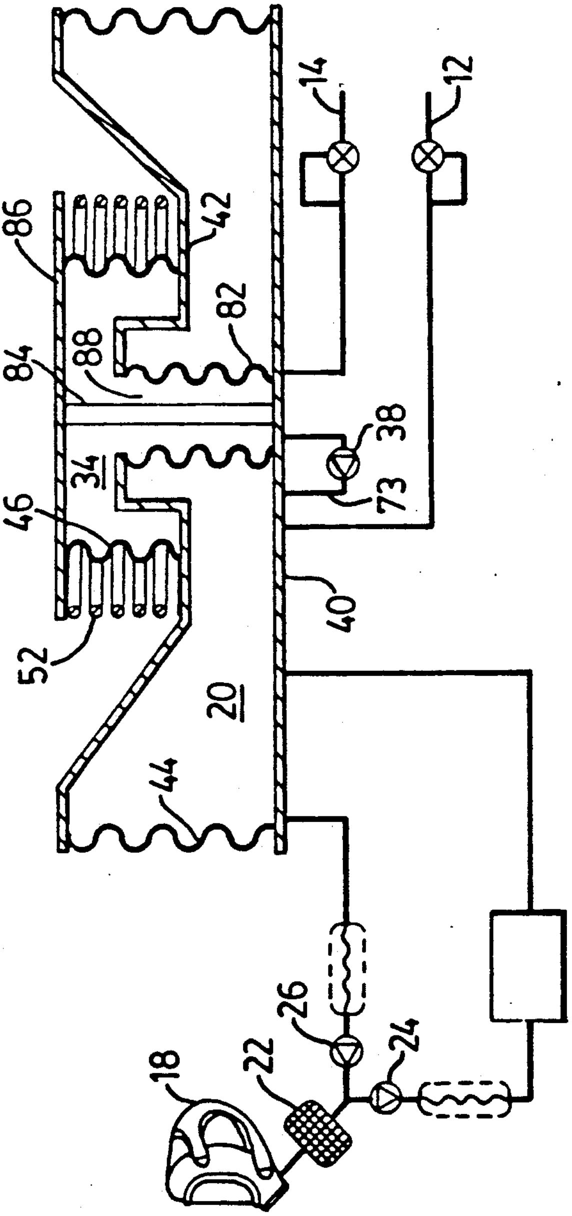
FIG. 5 shows a fifth embodiment of the first and second variable volume chambers of the present invention.

The embodiment shown in FIG. 5 is similar to that shown in FIG. 1 except that the second variable volume chamber 34 fluidly communicates with both sides of platen 42 through an opening 88. A third expansive cylinder 82 extends between the bottom of the platen 42 and the fixed bottom 40. Here the second expansive cylinder 46 is provided between the platen 42 and the top 86, with the spring 52 provided around the cylinder 46. The fixed top 86 can be the top of housing 48. Alternatively, as shown in FIG. 5, the fixed top 86 can be a disc-shaped member held in place by a locator rod 84 extending between the fixed top 86 and the fixed bottom 40. For this configuration to work it is necessary that the third expansive cylinder 82 be of a different and smaller diameter than the second expansive cylinder 46. Then, when the platen 42 moves downward, the volume of the second variable volume chamber 34 increases although the volume in the third expansive cylinder 82 is decreasing. If the cylinders were of the same diameter, as the height of the second variable volume chamber 34 remains constant, being defined by fixed top 86 and fixed bottom 40, movement of the platen 42 would not alter the volume of the second variable volume chamber 34.

In the embodiment illustrated in FIG. 5, removal of gas from chamber 20 during inhalation would cause platen 42 to be drawn toward the fixed bottom 40. This would cause an increase in the volume of the second variable volume chamber 34, drawing oxygen into this chamber. Subsequent exhalation would cause exhalate introduction into the first variable volume chamber 20 causing platen 42 to move toward the fixed top 86. Movement of the platen 42 toward the fixed top 86 decreases the volume of the second variable volume chamber 34 causing oxygen introduction into the first variable volume chamber 20 through external conduit 73. Thus, like FIG. 4, the chamber 34 is recharged during inhalation, and discharges oxygen into the respiratory circuit during exhalation.

As stated above, a variety of different oxygen and air supply systems can be used. Accordingly, the specific oxygen and air supply systems shown are only outlined briefly below.

The air supply system 12 includes a first conduit 90. At one end, the conduit 90 is connected to an air supply bottle 92 and to a fill port 94 for filling of the air supply bottle 92. A burst disc 96 is connected to the conduit 90, to prevent excess pressures arising in the conduit 90. The conduit 90 is connected through an air shut-off valve 98 to an air connector 100. An air gauge 102 is also connected to the first conduit 90.

From the connector 100, a second conduit 104 extends through an air regulator valve 106 to the air inlet 56. An air warning whistle 108 is connected either side of the air regulator 106, to provide an audible indication of low air pressure. A branch line 110 is connected through an orifice 112, connector 114 and a flexible hose 116 to a user visible pressure gauge 118.

The oxygen supply system 14 generally corresponds to the air supply system. Thus, it includes an oxygen bottle 120, oxygen fill port 122 and a burst disc 124 all connected to a first oxygen conduit 126. This conduit 126 is connected through an oxygen shut-off valve 128 to an oxygen connector 130. The oxygen shut-off valve 128 is connected to the air shut-off valve 98, so that they can only be operated together. The oxygen and air connectors 100, 130 are mounted together. An oxygen gauge 131, corresponding to the air gauge 102 is connected to the oxygen conduit 126.

The connector 130 is connected to a second oxygen conduit 132, which includes at its end two oxygen regulating valves 134, 136, an oxygen warning whistle 138 is connected across the first oxygen regulating valve 134. A user visible oxygen gauge 140 is connected by a flexible hose 142, connector 144 and orifice 146 to the second oxygen conduit 132. Filters 148 are provided in the second air and oxygen conduits 104, 132.

It is to be understood that what has been described are preferred embodiments of the invention and it is possible to make variations while staying within the scope of the invention.

An example of a variation which is within the scope of the present invention, is to provide an oxygen flow regulator and a respiratory flow transducer separate from the first variable volume chamber. This could be accomplished for example by the use of a constant displacement oxygen admitting pump linked to a metering device which monitors the breathing gas demand by the user. In such an embodiment the metering device would act as a respiratory flow transducer, the constant displacement oxygen admitting pump would act as the oxygen flow regulator and the linkage means between the meter and the pump would constrain the oxygen flow regulator to operate together with the meter.

We claim:

1. A respiratory apparatus for supplying breathing gas to a user, said apparatus comprising:

a respiratory circuit including a first variable volume chamber which contracts and expands during inhalation and exhalation respectively and which functions as a respiratory flow transducer subjected to the breathing gas demand by said user, a connection means for supplying breathing gas to and receiving exhaled gas from a user;

an oxygen flow regulator connected to said respiratory circuit for the introduction of oxygen and comprising a second variable volume chamber and a normally closed oxygen admission valve connected between the second variable volume chamber and the respiratory circuit, which valve opens in response to excess pressure in the second variable volume chamber to admit oxygen into said respiratory circuit; an oxygen supply inlet connected to said oxygen flow regulator; and, linkage means connecting said first and second variable volume chambers and constraining the first and second variable volume chambers to operate together, whereby there is a substantially constant ratio between the breathing gas flow rate and the oxygen flow rate.

2. An apparatus as claimed in claim 1, wherein said normally closed oxygen admission valve is connected between the first and second variable volume chambers, so that oxygen is admitted into the first variable volume chamber.

3. An apparatus as in claim 2 wherein said second variable volume chamber is contained within the said first variable volume chamber.

4. An apparatus as in claims 1, 2 or 3, which includes biasing means acting against said first variable volume chamber to urge said first variable volume chamber toward a reduced volume and thereby to ensure a positive pressure in said respiratory circuit relative to ambient pressure.

5. An apparatus as in claims 1, 2, or 3, further comprising an air bleed system, said air bleed system comprising:

an air flow controller connected into said respiratory circuit; an air supply inlet connected to said air flow controller; a normally closed vent valve connected to said respiratory circuit, said vent valve in its open position permitting exhaled gas to escape from said apparatus; and, actuator means connecting said vent valve with said first variable volume chamber to open said vent valve when said first variable volume chamber reaches a pre-determined maximum volume and to permit said vent valve to close when the volume in said first variable volume chamber decreases below said predetermined maximum volume.

6. An apparatus as in claim 1 further comprising an air bleed system, said air bleed system having;

an air flow controller connected to respiratory circuit; an air supply inlet connected to said air flow controller; a normally closed vent valve connected to said respiratory circuit, said vent valve in its open position permitting exhaled gas to escape from said apparatus; an actuator means connecting said vent valve with said first variable volume chamber to open said vent valve when said first variable volume chamber reaches a predetermined maximum volume and to permit said vent valve to close when the volume in said first variable volume chamber decreases below said predetermined maximum volume.

7. An apparatus as in claim 6, wherein said air flow controller is connected to the connection means.

8. An apparatus as in claim 7 wherein the connection means comprises a mask and an oral/nasal cup within the mask, with the oral/nasal cup connected into the respiratory circuit, and with the air flow controller connected to the mask.

9. An apparatus as in claim 6, further including a carbon dioxide remover connected to said respiratory circuit for removing carbon dioxide from said respiratory circuit.

10. An apparatus as in claim 9, which includes a regenerative heat exchanger, provided in the respiratory circuit adjacent the connection means, with the connection means being connected to the respiratory circuit via the regenerative heat exchanger, the regenerative heat exchanger, heating and humidifying exhaled gas and cooling and dehumidifying breathing gas.

11. An apparatus as in claim 10, wherein the respiratory circuit is circular, with gas flowing through each part of the respiratory circuit, with the exception of the heat exchanger and the connection means, in one direction, the gas also flowing through the carbon dioxide remover and the first variable volume chamber in one direction.

12. An apparatus as in claim 11, wherein the heat exchanger is connected to the respiratory circuit by non-return inhalation and exhalation valves. The inhalation valve only permitting gas to flow towards the heat exchanger, and the exhalation only permitting gas to flow away from the heat exchanger.

13. An apparatus as in claim 12, wherein the respiratory circuit includes a non-return valve, only permitting gas flow in the desired direction, and wherein the vent valve is connected to the respiratory circuit upstream from that non-return valve, whereby, when the vent valve is open, that non-return valve prevents backflow in the respiratory circuit.

14. An apparatus as in claim 6, 9, 11 or 12, which includes an air make-up system comprising a normally closed inlet valve connected to said air supply inlet and to the respiratory circuit, the air inlet valve admitting air into the respiratory circuit when open, an air inlet valve actuator connecting said air inlet valve with said first variable volume chamber, to open said air inlet valve when said first variable volume chamber reaches a predetermined minimum volume and to permit said air inlet valve to close when said first variable volume chamber exceeds said predetermined minimum volume.

15. An apparatus as in claim 5, which includes an air make-up air system comprising a normally closed inlet valve connected to said air supply and to the respiratory circuit, the air inlet valve admitting air into the respiratory circuit when open, an air inlet valve actuator connecting said air inlet valve with said first variable volume chamber, to open said air inlet valve when said first variable volume chamber reaches a predetermined minimum volume and to permit said air inlet valve to close when said first variable volume chamber exceeds said predetermined minimum volume.

16. An apparatus as in claim 6, 9 or 12, which includes a manually operable purge valve connected to the respiratory circuit, permitting the user to purge the respiratory circuit.

17. An apparatus as in claim 14, which includes a manually operable purge valve connected to the respiratory circuit, to permit the user to purge the respiratory circuit.

18. An apparatus as in claim 13, wherein the normally closed oxygen admission valve is connected between the first and second variable volume chambers, so that oxygen is admitted into the first variable volume chamber, and wherein the second variable volume chamber is contained within said first variable volume chamber.

19. An apparatus as in claim 18, wherein the first and second variable volume chambers have a common, fixed bottom, and a common platen opposite the fixed bottom, for movement towards and away from the fixed bottom, the first variable volume chamber includes a first expansive cylinder and the second variable volume chamber includes a second expansive cylinder, which expansive cylinders extent between the fixed bottom and the platen.

20. An apparatus as in claim 19, which includes a spring biasing means acting on the common platen, to maintain a positive pressure in the respiratory circuit.

21. An apparatus as in claim 20, wherein the first and second variable volume chambers are located within a common housing, with the spring biasing means acting between the housing and the platen, and the said fixed bottom forming part of the common housing.

22. An apparatus as in claim 21, wherein the normally closed vent valve is mounted on the housing opposite the fixed bottom and is actuated by displacement of the platen, and wherein the normally closed air inlet valve of the air make-up system is provided in said fixed bottom opening into the first variable volume chamber, and is actuated by movement of the platen towards the fixed bottom.

23. An apparatus as in claim 3, wherein the first and second variable volume chambers are defined by a common, fixed bottom at one end and a movable platen at the other end, the movable platen comprising a first, circular, central part closing off the second variable volume chamber and a second, annular outer part closing off the first variable volume chamber, the platen being generally cup-shaped with the second, annular part closer to the fixed bottom then the first, central part, the first variable volume chamber includes a first expansive cylinder and the second variable volume chamber includes a second expansive cylinder, which expansive cylinders extend between the fixed bottom and the platen.

24. An apparatus as in claim 23, wherein the respiratory circuit is circular and only permits gas flow in one direction and includes inhalation and exhalation valves connecting the connection means into the respiratory circuit, the inhalation valve only permitting gas flow towards the connection means and the exhalation valve only permitting gas flow away from the connection means, and wherein an inductor is provided upstream from the inhalation valve in the respiratory circuit, the inductor including an inlet for compressed air, for generating a positive pressure in the connection means, the exhalation valve including an offset equal to the positive pressure generated by the inductor.

25. An apparatus as in claim 23, which includes a tension spring mounted between the common bottom wall and the central part of the platen within the second variable volume chamber, for maintaining a positive pressure in the respiratory circuit.

26. An apparatus as in claim 3, wherein the first variable volume chamber is provided with a fixed bottom, the second variable volume chamber is mounted above the first variable volume chamber and includes a fixed top, and a movable platen is mounted between the fixed bottom and the top of the second variable volume chamber, closing off the first and second variable volume chambers, whereby when one of the first and second variable volume chambers expands, the other variable volume chamber contracts, the first variable volume chamber includes a first expansive cylinder extending between the fixed bottom and the platen and the second variable volume chamber includes a second expansive cylinder extending between the top of the second variable volume chamber and the platen.

27. An apparatus as in claim 24, 25 or 26 which includes: a carbon dioxide remover in the respiratory circuit for removing carbon dioxide; a heat exchanger mounted between the connection means and the respiratory circuit for heating and humidifying exhaled air and cooling and dehumidifying inhaled air; an air bleed system comprising an air flow controller connected into the respiratory circuit, and having an air supply inlet, a normally closed vent valve connected into the respiratory circuit and actuator means for opening the normally closed vent valve when the volume of the first variable volume chamber exceeds a predetermined maximum volume, to vent gas from the respiratory circuit; and a make-up air system connected to said first variable volume chamber and to said air inlet, said air make-up system having a normally closed air inlet valve connected to the air supply inlet, said air inlet valve in its open position admitting air into said first variable volume chamber an air inlet valve actuator connecting said air inlet valve with said first variable volume chamber to open said air inlet valve when said first variable volume chamber reaches a predetermined minimum volume and to close said air inlet valve when said first variable volume chamber exceeds said predetermined minimum volume.

28. An apparatus as claimed in claim 2 wherein said first variable volume chamber and said second variable volume chamber have a common fixed bottom at one end, said first variable volume chamber has a movable platen at the other end and a first expansive cylinder extending between the fixed bottom and the movable platen, said second variable volume chamber has a fixed top and said second variable volume chamber is defined by a second expansive cylinder extending between said platen and said fixed top, and by a third expansive cylinder extending between said fixed bottom and said movable platen and having a different cross-section from the second expansive cylinder, said platen having an opening fluidly connecting said first and second expansive cylinders, whereby movement of said platen toward either of said fixed top or said fixed bottom causes a change in volume of the second variable volume chamber.

29. An apparatus as in claim 28 which includes: a carbon dioxide remover in the respiratory circuit for removing carbon dioxide; a heat exchanger mounted between the connection means and the respiratory circuit for heating and humidifying exhaled air and cooling and dehumidifying inhaled air; an air bleed system comprising an air flow controller connected into the respiratory circuit, and having an air supply inlet, a normally closed vent valve connected into the respiratory circuit and actuator means for opening the normally closed vent valve when the volume of the first variable volume chamber exceeds a predetermined maximum volume, to vent gas from the respiratory circuit; and a make-up air system connected to said first variable volume chamber and to said air inlet, said air make-up system having a normally closed air inlet valve connected to the air supply inlet, said air inlet valve in its open position admitting air into said first variable volume chamber an air inlet valve actuator connecting said air inlet valve with said first variable volume chamber to open said air inlet valve when said first variable volume chamber reaches a predetermined minimum volume and to close said air inlet valve when said first variable volume chamber exceeds said predetermined minimum volume.

* * * * *